(12) United States Patent
Miljak

(10) Patent No.: US 7,031,862 B2
(45) Date of Patent: Apr. 18, 2006

(54) APPARATUS AND ANALYSIS METHOD FOR DETERMINATION OF MOISTURE IN MATERIALS

(75) Inventor: David Geoffrey Miljak, Jannali (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 10/482,733

(22) PCT Filed: Jul. 4, 2002

(86) PCT No.: PCT/AU02/00902

§ 371 (c)(1),
(2), (4) Date: Mar. 24, 2004

(87) PCT Pub. No.: WO03/005008

PCT Pub. Date: Jan. 16, 2003

(65) Prior Publication Data

US 2004/0210409 A1 Oct. 21, 2004

(30) Foreign Application Priority Data

Jul. 4, 2001 (AU) .................................. PR 6111

(51) Int. Cl.
*G01L 7/00* (2006.01)
*G01N 5/02* (2006.01)
(52) U.S. Cl. .......................... 702/100; 73/73; 324/640
(58) Field of Classification Search ................ 702/23, 702/30, 99, 179, 181, 188; 324/634, 637, 324/640, 664, 690, 639; 73/73, 865; 209/526, 209/546
See application file for complete search history.

(56) References Cited

U.S. PATENT DOCUMENTS

| | | | |
|---|---|---|---|
| 3,460,030 A | 8/1969 | Brunton et al. | 324/640 |
| 3,693,079 A | 9/1972 | Walker | 378/53 |
| 4,962,384 A | 10/1990 | Walker | 343/786 |
| 5,333,493 A | 8/1994 | Cutmore | 324/640 |
| 5,502,393 A | 3/1996 | Yamaguchi et al. | 324/639 |
| 5,767,685 A | 6/1998 | Walker | 324/640 |
| 5,845,529 A | 12/1998 | Moshe et al. | 73/73 |
| 6,107,809 A | 8/2000 | Moshe et al. | 324/640 |
| 6,249,129 B1 | 6/2001 | Burk et al. | 324/639 |

FOREIGN PATENT DOCUMENTS

DE 2 97 21 039 2/1998
EP 0 990 887 4/2000

OTHER PUBLICATIONS

Archibald et al. "Regression Analysis of Microwave Spectra for Temperature-Compensated and Density-Independent Determination of Wheat Moisture Content" *Society for Applied Spectroscopy*; vol. 52, 1998; pp 1435-1446.

(Continued)

*Primary Examiner*—Michael Nghiem
*Assistant Examiner*—John Le
(74) *Attorney, Agent, or Firm*—Nixon & Vanderhye, PC

(57) ABSTRACT

There is disclosed a method of estimating moisture content in a material involving directing a first frequency ($f_1$) signal and a second frequency ($f_2$) signal through a material, determining a first absolute phase shift ($\phi_1$) of the frequency signal and a second absolute phase shift ($\phi_2$) of the second frequency signal, transforming $\phi_1$ to a first corrected absolute phase shift ($\phi_{1c}$) and $\phi_2$ to a second corrected absolute phase shift ($\phi_{2c}$) in accordance with an expected relationship between $\phi_1$ and $\phi_2$, and estimating moisture content from $\phi_{1c}$ and $\phi_{2c}$.

34 Claims, 3 Drawing Sheets

OTHER PUBLICATIONS

Daschner et al. "Multiparameter Microwave Sensors for Determining Composition or Condition of Substances" *IEEE MTT-S Digest 2000*; pp 1567-1570.

European Search Report, for EP 02 74 2535, dated Sept. 1, 2005.

Cutmore, N., et al., "On-Conveyor Determination of Moisture in Coal", *Journal of Microwave Power and Electromagnetic Energy*, 26(4):237-242 (1991) (XP009050827).

Kupfer, K., "Mikrowellenfeuchtemeβgeräte und ihr Einsatz in der Prozeβtechnik", *Technisches Messen*, 61(11):409-420 (1994) (XP000479785).

Ebbe Nyfors and Pertti Vainikainen, "Industrial Microwave Sensors", Artech House, Boston, London, pp. 79-85 and 201-229 (1989) (XP002336359).

Miljak et al. "Low Cost On-line Microwave Moisture Analyser for the Minerals and Process Industries" Microwave Conference, 2000 Asia-Pacific (Sydney, Australia); pp. 89-93; Dec. 2000.

APPARATUS AND ANALYSIS METHOD FOR DETERMINATION OF MOISTURE IN MATERIALS

This application is the US national phase of international application PCT/AU02/00902 filed 4 Jul. 2002 which designated the U.S. and claims benefit of AU PR 6111, dated 4 Jul. 2001, the entire content of which is hereby incorporated by reference.

FIELD OF THE INVENTION

The present invention relates to a method and apparatus for determining the moisture content of materials.

BACKGROUND OF THE INVENTION

Moisture content is a key production parameter in many processes. Materials of interest are wide ranging and include food-stuffs, chemicals, mineral ores, mineral concentrates, coal, oil and gas. For some time it has been recognised that electromagnetic wave interaction with the material of interest may provide a method for moisture determination. Microwave-based methods rely on the observed high correlation between moisture content and either one or more of the parameters of wave phase shift, reflectance or attenuation. This correlation exists for a wide range of materials. Fundamentally the correlation occurs because unbounded water exhibits a dielectric constant with a very large magnitude compared to the material in which it is entrained. The effective dielectric constant may be derived from the dielectric tensor, which is the most general physical quantity that describes wave dispersion in all types of linear media, both magnetic and non-magnetic. In general the non-magnetic material response is dependent on both real and imaginary parts of the effective dielectric constant. However, the phase shift and reflectivity is usually mostly affected by the real part for typical materials of interest, while attenuation is more dependent on both real and imaginary parts. Similar considerations apply for magnetic materials, so long as the magnetic response remains somewhat weaker than the dielectric response imparted by the presence of free moisture.

Microwave methods may generally be divided between different classes of measurement. For example, measurements may employ the apparatus of tuned microwave resonant cavities. Another class of measurement involves free space measurements. In free space measurements-radiating structures (antennas) launch electromagnetic waves which are transmitted without the use of any guiding structure towards the material of interest. Free space methods have the general advantage that the apparatus does not constrain the flow of material in any way, which may be important in industrial processes. Free space measurements themselves may be generally subdivided between transmission and reflection measurements.

In reflection measurements the wave reflected off an air-material interface is measured. This wave may be received by the same structure that is used to transmit the wave, or with alternative receiving antennas. The amplitude and phase of the reflected wave is correlated in some way to the moisture content.

In transmission measurements, the waves are allowed to propagate through the material of interest from one side and are measured with a separate receiving antenna on the other side of the material layer. Either or both the phase shift and attenuation of the wave through the material may serve as the basic variable used to estimate moisture content, although phase shift generally demonstrates the better correlation to moisture content. However, phase shift and attenuation are also generally dependent on both the density and thickness of the material. Specifically, phase shift varies most linearly with the quantity defined by material mass per unit area (MPUA) presented to the transmitted wave. Because of inevitable variation of this quantity in most applications, an auxiliary or normalising parameter approximating MPUA is usually required to compensate for these variations. For example, MPUA may be approximated by either of the parameters of material height or mass loading. The auxiliary parameter is used to provide a weighting parameter to normalise the wave phase shift before moisture is inferred from the measurement. Where significant non-linearities exist between the weighting parameter and MPUA this will increase error in the estimated moisture content.

An important detail of free space transmission technology is the magnitude of phase shift imparted by the material. Often the phase shift is greater then 360 degrees. Since a single measurement of phase can only define the phase shift in the 0–360 degree range, measurements that rely on a single transmission frequency are often limited to materials that do not change markedly in presentation or moisture content. This fact limits the utility of single frequency measurements. Presently the state of the art in transmission measurements is to employ multi-frequency methods. There are several classes of multi-frequency method. One class employs two (dual) discrete frequencies separated by a modest frequency range (high frequency approximately 1.05 to 2 times the lower frequency). Another class employs a multitude of discrete frequencies or a continuum of frequencies within a frequency band; these may generally be regarded as "swept" frequency methods. Yet another class may employ electromagnetic wave pulses (in this case the finite length of the pulse implicitly defines the frequency band that is used by the generation of sidebands). In all cases the information carried in extra frequency components is used to resolve the absolute phase shift beyond 360 degrees.

Error in transmission measurements may derive from a number of sources. One source of error is the reception of spurious waves with phase that may be unrelated or weakly related to the moisture in the material. Such spurious waves include waves reaching the receiver that have not passed through the material (or only a small section of material), and waves which pass several times through the material by way of multiple reflections. These spurious waves act to distort the measured phase in all types of transmission measurements. Another source of error may be from limitations in the receiver itself. For example the receiver may lose sensitivity at high attenuation, resulting in the measurement of phase that is not a true representation of the actual received wave phase.

It would be desirable to provide an improved technique for estimating moisture content.

SUMMARY OF THE INVENTION

Accordingly, the invention provides a method of estimating moisture content in a material including:

directing a first frequency ($f_1$) signal and a second frequency ($f_2$) signal through a material;

determining a first absolute phase shift ($\phi_1$) of said first frequency signal and a second absolute phase shift ($\phi_2$) of said second frequency signal;

transforming $\phi_1$ to a first corrected absolute phase shift ($\phi_{1c}$) and $\phi_2$ to a second corrected absolute phase shift ($\phi_{2c}$) in accordance with an expected relationship between $\phi_1$ and $\phi_2$; and estimating moisture content from $\phi_{1c}$ and $\phi_{2c}$.

Preferably, said expected relationship is $\phi_1 = K\phi_2 f_1/f_2$, where K is a constant that takes into account dispersion of the material at the two frequencies.

Preferably, transforming said first and second absolute phase shifts is performed using the following transformations, where $\gamma$ is a fixed constant:

$$\phi_{2c} = \frac{\phi_2 + \gamma\phi_1}{1+\gamma^2}$$

$$\phi_{1c} = \gamma\phi_{2c}$$

Preferably, $f_1$ and $f_2$ are chosen so that K is close to 1.0.

Preferably, $f_1$ and $f_2$ are in the range of 0.5 to 2.0 GHz.

The invention also provides a method of estimating moisture content in a material involving:

(a) obtaining measured data including measured phase data, actual moisture content data, and weighting data, where the weighting data is representative of the material mass per unit area of the material for which moisture content is to be estimated;

(b) setting up a first modelling function to model any non-linearity in said weighting data, said first modelling function having a first set of coefficients;

(c) setting up a second modelling function relating estimated moisture content to measured phase and said first modelling function, said second modelling function having a second set of coefficients;

(d) determining values of said first and second sets of coefficients which minimise error between estimated moisture content and actual moisture content for said measured data; and (e) estimating moisture content using said first and second modelling functions with said determined values of said first and second sets of coefficients.

Preferably, step (d) involves (i) determining a plurality of sets of trial values for said first set of coefficients, (ii) performing a regression to determine values of said second set of coefficients which minimise error for each set of trial values; and (iii) determining which set of trial values minimises error.

Preferably step (d)(i) is performed using a non-linear minimisation scheme.

Preferably, said non-linear minimisation scheme is the Nelder-Mead downhill simplex method.

Preferably said first modelling function is in the form $w^* = G(w,B)$, where $w^*$ is the modelled weighting, $w$ is the actual weighting and B represents the first set of coefficients.

Preferably, $G(w,B)$ is chosen to most closely model non-linearity in w.

In one embodiment, $G(w,B)$ may equal $b_1 + b_2 w + b_3 w^2$ where the first set of coefficients, $B = \{b_1, b_2, b_3\}$.

Preferably, said second modelling function is a set of functions, in the form $$M^* = \sum_{i=1}^{n} C_i F_i$$

where $M^*$ is estimated moisture content, $C_i$ represent a set of n second coefficients and, $F_i$ represents a set of functions.

Preferably, said set of function $F_i$ are functions of measured phase ($\phi$) and said first modelling function $w^*$.

Preferably, n=3 and $$F(\phi, w^*) = \left\{ 1, \frac{\phi}{\omega^*}, \frac{\phi^2}{\omega^{*2}} \right\}$$

It will be apparent that the above methods can be combined to estimate moisture content of a material.

DESCRIPTION OF THE PREFERRED EMBODIMENT

The preferred embodiment of the present invention is a method which employs a dual discrete frequency free space transmission apparatus that is used to measure continuously the phase shifts and attenuations of electromagnetic waves at each frequency that are propagated through the material of interest. The preferred embodiment exploits the discovery of an analysis technique, hereafter referred to as method (I), involving the use of two measured phases that provides a superior accuracy of moisture measurement. Specifically, a transformation involving two measured phases is used to calculate a correction so as to obtain a more accurate absolute phase shift by reducing the effect of spurious waves and receiver errors. Secondly, the preferred embodiment exploits a compensation technique, henceforth known as method (II), during device calibration to improve measurement accuracy. This method (II) method is used to reduce distortions in an auxiliary weighting parameter (described above) required to normalise the measured phase shift.

A special configuration of apparatus is employed to facilitate the use of method (I), namely:

(i) the operation of the apparatus at low microwave frequency (approximately 0.5–2 GHz) so as to avoid dispersion effects imparted by materials;

(ii) at each measurement (carrier) frequency, the configuration of a quadrature modulator to provide single side-band (SSB) modulation of a microwave carrier at a suitably chosen intermediate frequency (IF);

(iii) for each measurement frequency, the generation of appropriate phase balanced and stable modulating signals provided to the modulator in (ii), so as to provide a suitably high level of suppression of the unwanted sideband in the SSB modulation;

(iv) for each measurement frequency, the configuration of a receiver to demodulate the received signal to a single analog signal at the IF frequency, with suitably applied low noise factor; and (v) at each measurement frequency, the logarithmic demodulation of the intermediate frequency in signal (iv), which provides two continuous signals each proportional to phase and the logarithm of amplitude.

The apparatus in this particular configuration specifically aids the implementation of method (I) through the high accuracy of phase measurement provided by this configuration. With inferior phase accuracy the error in moisture estimates is generally increased. In turn, the error reduction afforded by method (I) is reduced. While method (I) can be used with other apparatus, the value of method (I) is fully utilised and overall performance of the apparatus is enhanced if systematic and random phase errors related to the microwave receive circuitry are reduced.

Figure 3:
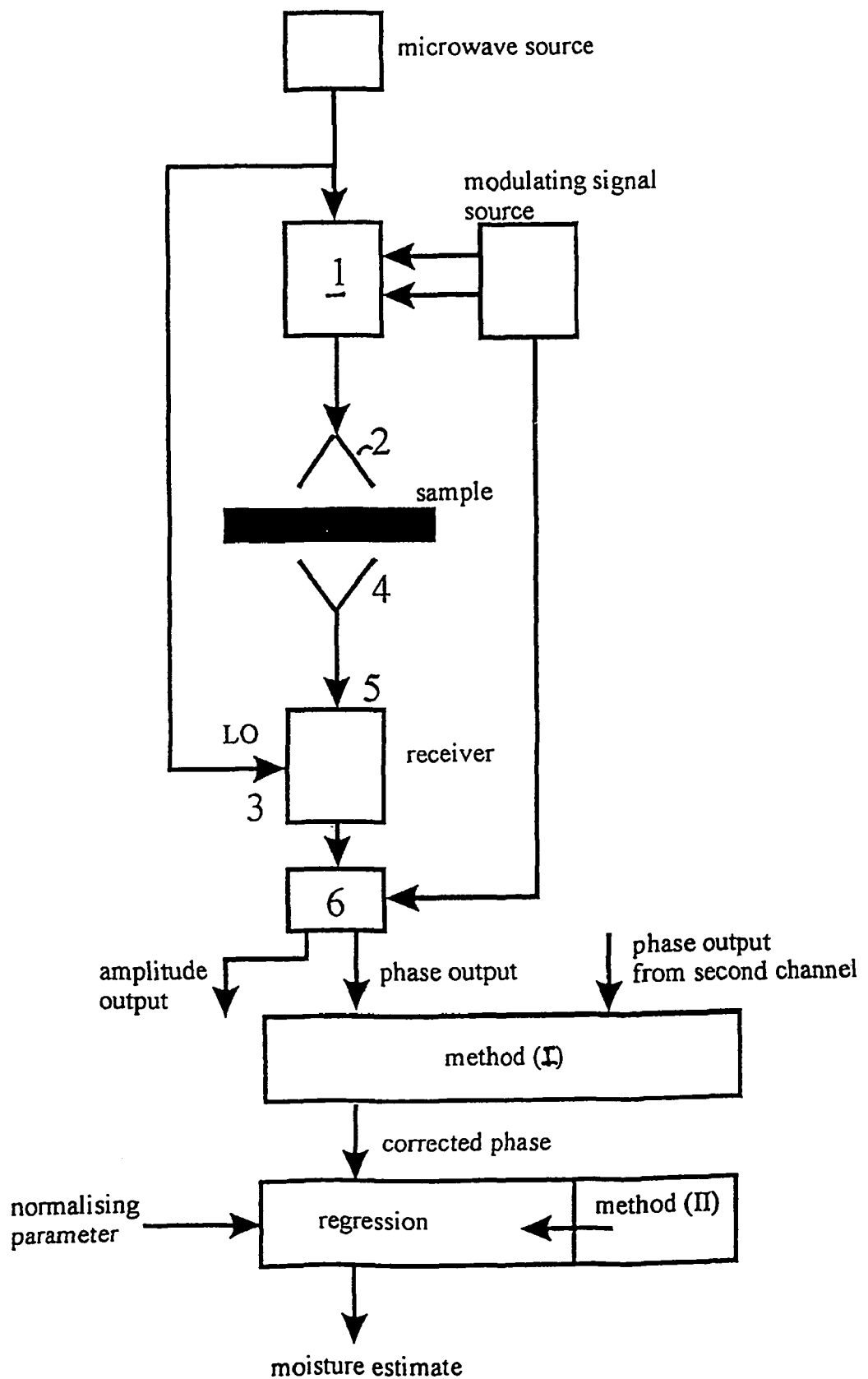
FIG. 3 shows typical apparatus for carrying out the methods of preferred embodiments of the present invention.

An example of a preferred configuration of the apparatus used to implement the high accuracy phase measurement scheme is shown in block diagram form in FIG. 3, where one channel of the transmit-receive system is shown. The device would normally have two transmit-receive channels at separate frequencies, each operating continuously. Modulating signals, together with the carrier at microwave frequency, are applied to a quadrature modulator 1. The modulating frequency may lie anywhere between audio and high frequency radio bands. Two waves at microwave frequency are therefore available to the channel; the original carrier and the output of the quadrature modulator. One of these waves may be propagated through the material (probe wave) after being launched from a transmitting antenna 2, while the other may be used as a local oscillator in a receiver subsystem 3. Upon reception of the probe wave by a receiving antenna 4, the probe wave is fed to the low-noise demodulating receiver 5. A component of the receiver output will be in the same frequency band as the modulating signals. This output wave may be compared to one of the modulating signals (either serving as a possible reference wave) in order to determine phase shift and attenuation imparted to the microwave probe wave. A direct reading of the phase and amplitude is provided using a phase comparator and a logarithmic demodulator 6. In general, accuracy of the method depends on the amount of suppression of unwanted sidebands generated by the modulator. Generally quadrature modulators have imperfections that produce small but non-zero unwanted sidebands. However very high sideband suppression (greater than 50 decibels compared to the carrier) in this system is afforded through a specific choice and generation of modulating signals. This in turn leads to high phase accuracy e.g., less than 0.5 degree phase accuracy over an entire 360 degree phase range.

In its simplest form method (I) may be described as follows. Let $\phi_1$ and $\phi_2$ be the absolute phase shifts measured at the two respective discrete frequencies $f_1$ and $f_2$. The absolute phases are calculated from the measured phases using methods known to persons skilled in the art. The following transformation may then be used to determine corrected phases $\phi_{1c}$ and $\phi_{2c}$:

$$\phi_{2c} = \frac{\phi_2 + \gamma \phi_1}{1 + \gamma^2} \quad (1)$$

$$\phi_{1c} = \gamma \phi_{2c}$$

The parameter $\gamma$ is a fixed constant with a value suitably chosen so as to reduce measurement error. Persons skilled in the art will appreciate that other transformations linearly related to equation (1) may also be used to the same effect.

After application of this correction procedure the corrected phases at each operating frequency are linearly related, and therefore either corrected phase can be used to the same effect in a regression that determines predicted moisture. The reduction in measurement error afforded by this transformation (and the consequent improvement in the quality of the regression) depends on the value of $\gamma$ chosen and the distribution of phase errors. A particular value of $\gamma$ found to be suitable may be derived as follows. In the loss-free case the theoretical relationship between the absolute phase of two waves is given by:

$$\phi_1 = K \phi_2 f_1 / f_2, \quad (2)$$

where K is a fixed parameter for a given pair of frequencies that takes into account dispersion of the material at the two frequencies. A similar but more complicated equation may be derived in the high-loss case. In practice the measured phases do not obey this relation because of the presence of spurious waves or errors due to the phase detector used. A particular choice of $\gamma$ that forces the corrected phases to obey equation (2) is $\gamma = K f_1 / f_2$. This prescription for $\gamma$ therefore yields corrected phases with ratio most closely related to that expected from theory, and therefore provides a significant reduction in the effect of spurious waves. However other values of $\gamma$ may provide similar error reduction.

The reduction in measurement error afforded by the transformation defined by equation (1) also depends on the distribution of phase errors. For example, the following error distribution may be assumed:

$$(\phi_{T1} - \phi_1, \phi_{T2} - \phi_2)_i = (\epsilon_i \cos \theta_i, \epsilon_i \sin \theta_i), \quad (3)$$

where $\phi_{T1}$, $\phi_{T2}$ are the true phase shifts at $f_1$ and $f_2$ respectively, and $\phi_1$, $\phi_2$ are the corresponding measured phase shifts. The subscript i denotes sample number. The variables $\epsilon$ and $\theta$ are used to model an assumed error distribution. For the purposes of this example $\gamma = K f_1 / f_2$. If over a large number of samples $\theta$ is uniformly distributed and $\epsilon$ normally distributed around a mean of zero, then the transformation yields a revised error that is 70% the value of the uncorrected error. This reduction typically accounts for a similar reduction in the uncertainty of the moisture estimate, thereby providing a superior measurement. If the phases have fixed offsets, due for example to changes in transmission coefficient at the material-belt interface, then estimates of the offset obtained by other means may be included in the scheme to retain the full benefit of uncertainty reduction. It is noted that this correction procedure does not require knowledge of the moisture of the material. Method (I) is important for the operation of the apparatus since it affords significant error reduction in on-line applications, and is not merely a post-acquisition method useful only in off-line laboratory measurements. The method is aided by operating at low frequency so that the parameter K is often very near unity for many materials; this allows application of the method without recourse to complicated measurements to determine K. Furthermore the simultaneous measurement of the wave phase and amplitude at two frequencies and sufficiently high accuracy delivered by the apparatus is required for proper application of method (I).

Further to this application of the correction technique is the technique of compensation (method II) applied to an external weighting signal w that is usually provided to normalise measured phase, e.g., conveyor mass loading cell, mass flow meters in pipes etc. This is required since to a good approximation the moisture content is dependent on phase shift normalised to the material mass per unit area (MPUA). The auxiliary parameter w is used indirectly to infer relative MPUA. The technique described here may be used to remove to some extent the non-linearity that often exists between the parameter w and the material MPUA. As an example, it is assumed that calibration data is available where the pair of variables (φ,w) are the measured phase and weighting variable respectively, and M the corresponding actual moisture measured through some means, for example manual sampling. A conventional method of fitting involves fitting the set of measurements M to the measured phases and weightings (φ,w) using a set of basis functions F involving (φ,w):

$$M \Leftrightarrow \sum_{i=1}^{3} A_i F_i, A = \{a_1, a_2, a_3\}, F(\phi, w) = \left\{1, \frac{\phi}{w}, \frac{\phi^2}{w^2}\right\}. \quad (4)$$

In the example above it is assumed that the set A contains three elements and that the form for F is quadratic in φ/w, where the symbol ⇔ denotes the least squares fitting operation for the unknown set of coefficients A. Here it is assumed that a square or overdetermined system is established where the number of measurements equals or exceeds the number of required coefficients. In turn, a predicted moisture M* may be calculated from the measured phase φ using the derived set of coefficients A:

$$M^*(\phi, w) = \sum_{i=1}^{3} A_i F_i \quad (5)$$

A one to one correspondence between M and M* is therefore defined for each value of (φ,w). The quality of this regression may be defined by the standard deviation of differences between A and M* defined for each (φ,w). This quantity may be denoted as the standard error.

An improved scheme described here (method II) may be employed where there is significant variation in the parameter w. The parameter w is replaced by w*, where w* is determined by the dependence w*=G(w,B), where G is a function involving w and a first coefficient set B. This function G(w,B) is set up to model any non-linearity in w. The function G may be quite generally defined and may depend non-linearly on parameters in B. G should be chosen so as to most accurately model the supposed underlying non-linearity. As a simple example a quadratic functional form for G may be assumed involving three coefficients, but any number greater than one may be used.

$$w^* = G(w, B) = b_1 + b_2 w + b_3 w^2, B = \{b_1, b_2, b_3\} \quad (6)$$

As in the usual case, a regression may be performed but with w* replacing w, and a second set of coefficients C defining the regression may be obtained $$M^* = \sum_{i=1}^{3} C_i F_i \quad C = \{c_1, c_2, c_3\} \quad F(\phi, w^*) = \left\{1, \frac{\phi}{w^*}, \frac{\phi^2}{w^{*2}}\right\} \quad (7)$$

In this particular case degeneracy between coefficient set B and C must be removed by setting, for example, $b_2$ to unity. The first set of coefficients B are determined by a multi-dimensional non-linear minimisation scheme, e.g. the Nelder-Mead downhill simplex method, although any suitable minimisation scheme will suffice. For each trial value of first set B in the minimisation, the second set C and therefore the standard error of the regression is determined by the usual known least squares method described above. The standard error is the variable that is the object of minimisation. The multi-dimensional scheme is used to search the parameter space spanned by the first coefficient set B in order to find the optimal first set B that minimises the standard error. The second set C corresponding to the optimum is determined simultaneously and, if significant non-linearity exists between w and MPUA, the first and second sets B and C together describe a regression with a reduced standard error compared to that which would be obtained without the introduction of the first set B. Note that in general the function G must be chosen to adequately simulate the non-linearity in w in order to reduce the standard error.

Compensation method (II) provides a fitting technique that removes non-linearity between the parameter and MPUA. This formulation of a non-linear fitting method is straightforward, avoids strong redundancies between coefficients and has the advantage of transparency compared to the usual application of say, neural networks. The method can be performed off-line during measured calibration or may be implemented on-line in special circumstances where calibration data may be available to the device on-line.

EXAMPLES

A. Method (I)

Figure 1A:
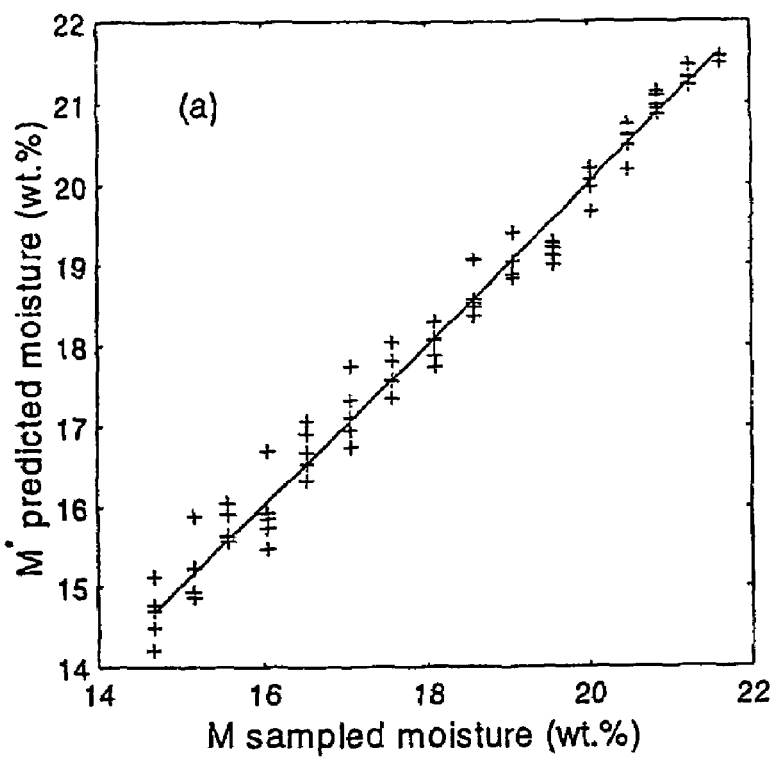
FIG. 1a shows a standard regression.
Figure 1B:
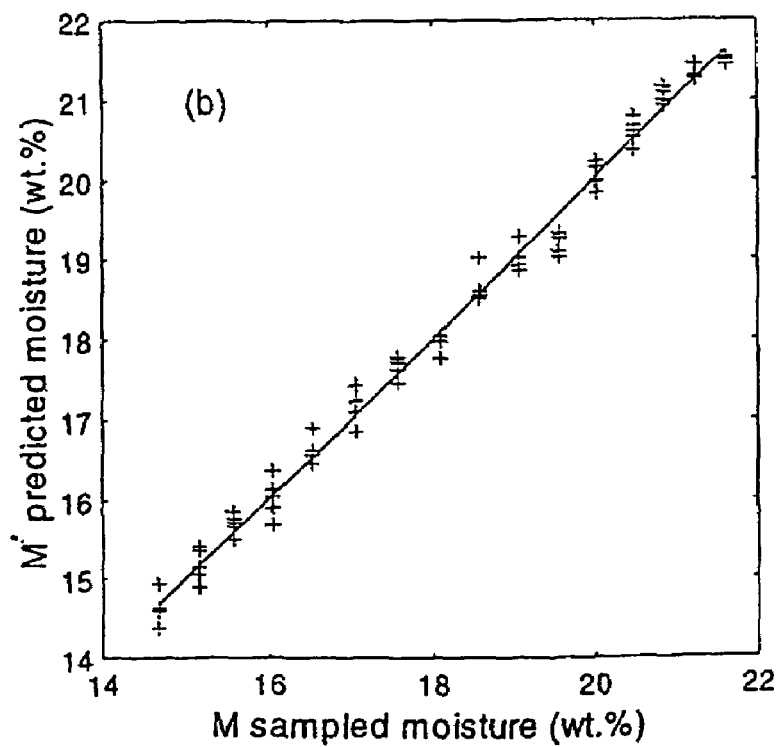
FIG. 1b shows a regression following the correction technique of the preferred embodiment.

Method (I) has been applied to a set of phase data measured in the laboratory for semi-bituminous coal for thickness spanning the range between 200–400 mm and moisture in the range 14.5–21.5 wt. %. FIG. 1(a) shows the regression obtained by fitting a quadratic between sampled moisture data M and Φ, where Φ is the phase at high frequency normalised to the material mass. In this case the sample mass is a good estimator of mass per unit area, since in the experiment the material filled a container of fixed cross sectional dimension. The standard error of the fit is 0.27 wt. % while the correlation coefficient is 0.990. The regression is defined by $M^* = -41.12 + 7.808\Phi - 0.2425\Phi^2$, where M* is the predicted moisture. A similar procedure may be separately performed for the low frequency phase data; in this case the standard error is 0.31% and correlation coefficient is 0.992. However, FIG. 1(b) shows the case where the correction procedure has been implemented, where $\gamma = Kf_1/f_2$, $K=1$ and $f_1/f_2=0.76$. That is, the phase has been modified according to equation (1) before performing the regression. The subsequent regression using the modified high frequency phases yields a standard error of 0.19% and a correlation coefficient of 0.996. The improved regression is defined by $M^* = -45.61 + 8.547\Phi - 0.2719\Phi^2$.

B. Method (II)

Figure 2A:
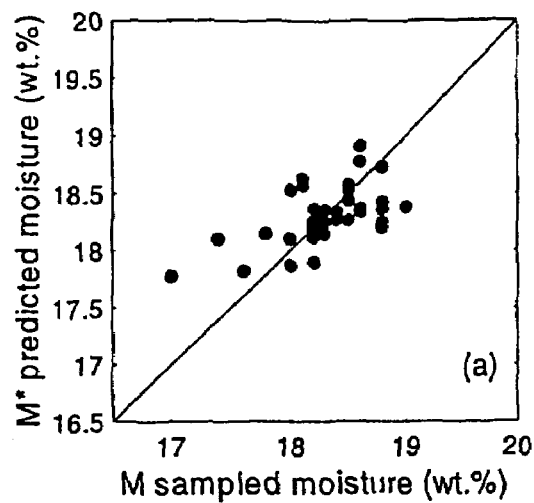
FIG. 2a shows a standard regression.

Method (II) was applied to data collected in an on-line application. A calibration consisting of a set containing 37 points was available to the method. For each sampled moisture M a measurement of the pair of variables (φ,w) was available for the fit, where φ is the absolute phase and w a normalising parameter, in this case derived from a belt-weigher. The variation in w over the calibration set was sufficient to merit use of method (II). The regression resulting without application of method (II) is shown in FIG. 2(a).

The standard error is 0.33%, where the regression has been performed using the relation $$M \Leftrightarrow \sum_{i=1}^{3} A_i F_i, \quad A = \{a_1, a_2, a_3\}, \quad F(\phi, w) = \left\{1, \frac{\phi}{w}, \frac{\phi^2}{w^2}\right\},$$

$$M^*(\phi, w) = \sum_{i=1}^{3} A_i F_i,$$

where M* is the predicted moisture and $a_1=3.690$, $a_2=7.468 \times 10^3$ and $a_3=-8.295 \times 10^5$. Coefficient set A was obtained using standard least squares analysis, as denoted by the operator $\Leftrightarrow$.

In the implementation of method (II) the underlying relation between w and MPUA, denoted by w*, was assumed to be of the form $$w^* = b_1 + w + b_2 w^2, \quad B = \{b_1, b_2\}.$$

Figure 2B:
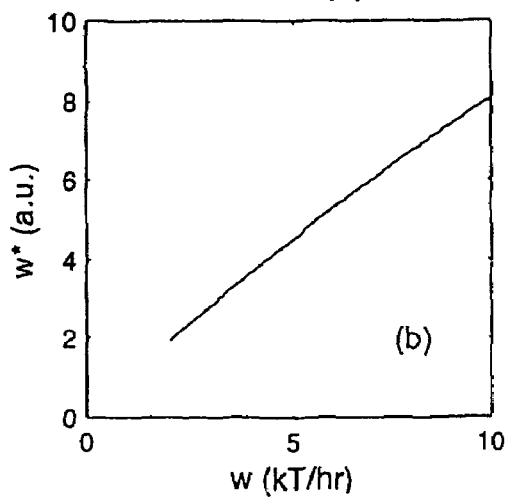
FIG. 2b shows how non-linearity in the weighting can be taken into account.
Figure 2C:
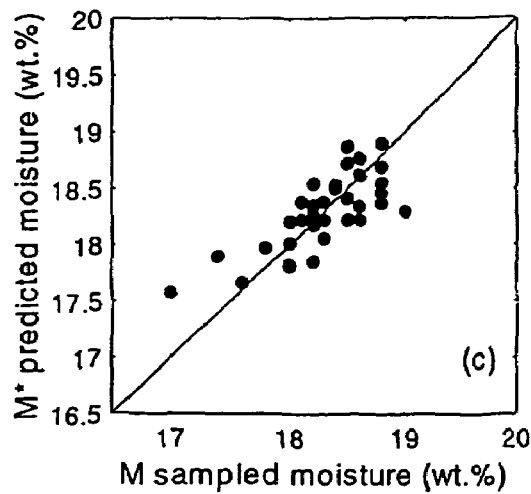
FIG. 2c shows predicted moisture plotted relative to sample moisture.

The Nelder-Mead minimisation of the standard error returned coefficients $b_1 = -178.0$ and $b_2 = 1.925 \times 10^{-5}$. The derived relation between w* and w is shown in FIG. 2(b). The revised regression equation was simultaneously provided:

$$M^* = \sum_{i=1}^{3} C_i F_i, \quad C = \{c_1, c_2, c_3\}, \quad F(\phi, w^*) = \left\{1, \frac{\phi}{w^*}, \frac{\phi^2}{w^{*2}}\right\},$$

where $c_1 = -15.80$, $c_2 = 1.680 \times 10^4$ and $c_3 = -1.943 \times 10^6$. Upon implementation of method (II) the standard error was reduced to 0.27%, with the regression plotted in FIG. 2(c).

It will be apparent to persons skilled in the art that various modifications can be made to the preferred embodiment without departing from the scope of the invention.

The invention claimed is:

1. A method of estimating moisture content in a material comprising:
   directing a first frequency ($f_1$) signal and a second frequency ($f_2$) signal through a material;
   determining a first absolute phase shift ($\phi_1$) of said first frequency signal and a second absolute phase shift ($\phi_2$) of said second frequency signal;
   transforming $\phi_1$ to a first corrected absolute phase shift ($\phi_{1c}$) and $\phi_2$ to a second corrected absolute phase shift ($\phi_{2c}$) in accordance with an expected relationship between $\phi_1$ and $\phi_2$, wherein said expected relationship is $\phi_1 = K \phi_2 f_1/f_2$, where K is a constant that takes into account dispersion of the material at the first and second frequencies; and
   estimating moisture content from $\phi_{1c}$ and $\phi_{2c}$.

2. A method as claimed in claim 1, wherein said step of transforming said first and second absolute phase shifts is performed using the transformations:

$$\phi_{2c} = \frac{\phi_2 + \gamma \phi_1}{1 + \gamma^2}$$

$$\phi_{1c} = \gamma \phi_{2c}$$

where $\gamma$ is a fixed constant.

3. A method as claimed in claim 2, wherein $\gamma = K f_1/f_2$.

4. A method as claimed in claim 3, wherein $f_1$ and $f_2$ are both in the range of 0.5 to 2.0 GHz.

5. A method as claimed in claim 1, wherein the frequencies $f_1$ and $f_2$ are used in said directing step are chosen so that K is close to 1.0.

6. A method as claimed in claim 1, wherein said step of estimating moisture content is performed using first and second modelling functions with determined values of first and second sets coefficients which are obtained by
   (a) obtaining measured data including measured phase data, actual moisture content data, and weighting data, where the weighting data is representative of the material mass per unit area of the material for which moisture content is to be estimated;
   (b) setting up a first modelling function to model any non-linearity in said weighting data, said first modelling function having a first set of coefficients;
   (c) setting up a second modelling function relating estimated moisture content to measured phase and said first modelling function, said second modelling function having a second set of coefficients; and
   (d) determining values of said first and second sets of coefficients which minimise error between estimated moisture content and actual moisture content for said measured data.

7. A method as claimed in claim 6, wherein step (d) involves:
   (i) determining a plurality of sets of trial values for said first set of coefficients;
   (ii) performing a regression to determine values of said second set of coefficients which minimise error for each set of trial values; and
   (iii) determining which set of trial values minimises error.

8. A method as claimed in claim 7, wherein step (d)(i) is performed using a non-linear minimisation scheme.

9. A method as claimed in claim 8, wherein said non-linear minimisation scheme is the Nelder-Mead downhill simplex method.

10. A method as claimed in claim 6, wherein said first modelling function is in the form w*=G(w,B), where w* is the modelled weighting, w is the actual weighting and B represents the first set of coefficients.

11. A method as claimed in claim 10, wherein G(w,B) is chosen to most closely model non-linearity in w.

12. A method as claimed in claim 10, wherein G(w,B) may equal $b_1 + b_2 w + b_3 w^2$ where the first set of coefficients, $B = \{b_1, b_2, b_3\}$.

13. A method as claimed in claim 6, wherein said second modelling function is a set of functions, in the form $$M^* = \sum_{i=1}^{n} C_i F_i$$

where M* is estimated moisture content, $C_i$ represent a set of n second coefficients and, $F_i$ represents a set of functions.

14. A method as claimed in claim 13, wherein said first modeling function is in the form w*=G(w,B), where w* is the modeling weighting, w is the actual weighting and B represents the first set of coefficients, and said set of function $F_i$ are functions of measured phase ($\phi$) and said first modelling function.

15. A method as claimed in claim 14, wherein n=3 and $$F(\phi, w^*) = \left\{1, \frac{\phi}{\omega^*}, \frac{\phi^2}{\omega^{*2}}\right\}.$$

16. Apparatus configured to perform the method of claim 1.

17. A method of estimating moisture content in a material comprising:
(a) obtaining measured data including measured phase data, actual moisture content data, and weighting data, where the weighting data is representative of the material mass per unit area of the material for which moisture content is to be estimated;
(b) setting up a first modelling function to model any non-linearity in said weighting data, said first modelling function having a first set of coefficients;
(c) setting up a second modelling function relating estimated moisture content to measured phase and said first modelling function, said second modelling function having a second set of coefficients;
(d) determining values of said first and second sets of coefficients which minimise error between estimated moisture content and actual moisture content for said measured data; and
(e) estimating moisture content using said first and second modelling functions with said determined values of said first and second sets of coefficients.

18. A method as claimed in claim 17, wherein step (d) comprises:
(i) determining a plurality of sets of trial values for said first set of coefficients;
(ii) performing a regression to determine values of said second set of coefficients which minimise error for each set of trial values; and
(iii) determining which set of trial values minimises error.

19. A method as claimed in claim 18, wherein step (d)(i) is performed using a non-linear minimisation scheme.

20. A method as claimed in claim 19, wherein said non-linear minimisation scheme is the Nelder-Mead downhill simplex method.

21. A method as claimed in claim 17, wherein said first modelling function is in the form w*=G(w,B), where w* is the modelled weighting, w is the actual weighting and B represents the first set of coefficients.

22. A method as claimed in claim 21, wherein G(w,B) is chosen to most closely model non-linearity in w.

23. A method as claimed in claim 21, wherein G(w,B)= $b_1+b_2w+b_3w^2$, where the first set of coefficients, B={$b_1$, $b_2$, $b_3$}.

24. A method as claimed in claim 17, wherein said second modelling function is a set of functions, in the form $$M^* = \sum_{i=1}^{n} C_i F_i$$

where M* is estimated moisture content, $C_i$ represent a set of n second coefficients and, $F_i$ represents a set of functions.

25. A method as claimed in claim 24, wherein said first modeling function is in the form w*=G(w,B), where w* is the modeling weighting, w is the actual weighting and B represents the first set of coefficients, and said set of functions $F_i$ are functions of measured phase ($\phi$) and said first modelling function.

26. A method as claimed in claim 25, wherein n=3 and $$F(\phi, w^*) = \left\{1, \frac{\phi}{\omega^*}, \frac{\phi^2}{\omega^{*2}}\right\}.$$

27. Apparatus configured to perform the method of claim 17.

28. Apparatus for estimating moisture content in a material, including:
a transmitter for directing a first frequency ($f_1$) signal and a second frequency ($f_2$) signal through a material;
a receiver for receiving said first and second frequency signals;
determining means for determining a first absolute phase shift ($\phi_1$) of said first frequency signal and a second absolute phase shift ($\phi_2$) of said second frequency signal;
transformation means for transforming $\phi_1$ to a first corrected absolute phase shift ($\phi_{1c}$) and $\phi_2$ to a second corrected absolute phase shift ($\phi_{2c}$) in accordance with an expected relationship between $\phi_1$ and $\phi_2$, wherein said expected relationship is $\phi_1$=K$\phi$2$f_1$/$f_2$, where K is a constant that takes into account dispersion of the material at the first and second frequencies; and
moisture content estimating means for estimating moisture content from $\phi_{1c}$ and $\phi_{2c}$.

29. Apparatus as claimed in claim 28, wherein said transformation means transforms said first and second absolute phase shifts is performed using the transformations:

$$\phi_{2c} = \frac{\phi_2 + \gamma\phi_1}{1+\gamma^2}$$

where γ is a fixed constant.

30. Apparatus as claimed in claim 29, γ=K$f_1$/$f_2$.

31. Apparatus as claimed in claim 28, wherein the frequencies $f_1$ and $f_2$ are chosen so that K is close to 1.0.

32. Apparatus as claimed in claim 31, wherein $f_1$ and $f_2$ are both in the range of 0.5 to 2.0 GHz.

33. Apparatus as claimed in claim 28, wherein said moisture content estimating means is calibrated by:
(a) obtaining measured data including measured phase data, actual moisture content data, and weighting data, where the weighting data is representative of the material mass per unit area of the material for which moisture content is to be estimated;
(b) setting up a first modelling function to model any non-linearity in said weighting data, said first modelling function having a first set of coefficients; and
(c) setting up a second modelling function relating estimated moisture content to measured phase and said first modelling function, said second modelling function having a second set of coefficients; and
(d) determining values of said first and second sets of coefficients which minimise error between estimated moisture content and actual moisture content for said measured data,
whereby said moisture content estimating means can estimate moisture content using said first and second modelling functions with said determined values of said first and second sets of coefficients.

34. Apparatus for estimating moisture content in a material, comprising:
- a transmitter for directing a first frequency ($f_1$) signal and a second frequency ($f_2$) signal through a material; and
- a receiver for receiving said first and second frequency signals,
- wherein the apparatus is configured to determine a first absolute phase shift ($\phi_1$) of the first frequency signal and a second absolute phase shift ($\phi_2$) of the second frequency signal; to transform $\phi_1$ to a first corrected absolute phase shift ($\phi_{1c}$) and $\phi_2$ to a second corrected absolute phase shift ($\phi_{2c}$) in accordance with an expected relationship between $\phi_1$ and $\phi_2$, wherein the expected relationship is $\phi_1 = K\phi_2 f_1/f_2$ and K is a constant that takes into account dispersion of the material at the first and second frequencies; and to estimate moisture content from $\phi_{1c}$ and $\phi_{2c}$.

* * * * *